United States Patent [19]

Lisle et al.

[11] Patent Number: 5,056,164
[45] Date of Patent: Oct. 15, 1991

[54] VISOR CAP AND EYE GLASS ORGANIZATION

[76] Inventors: Tommy W. Lisle, 806 N. Franklin, Sand Springs, Okla. 74063; Bill L. Lisle, 2813 E. El Paso St., Broken Arrow, Okla. 74014

[21] Appl. No.: 493,638

[22] Filed: Mar. 15, 1990

[51] Int. Cl.$^5$ .............................................. A61F 9/02
[52] U.S. Cl. ...................................... 2/453; 2/185 R; 2/DIG. 6
[58] Field of Search ................ 2/162, 10, DIG. 6, 453, 2/199, 185 R; 351/155

[56] References Cited

U.S. PATENT DOCUMENTS

| | | | |
|---|---|---|---|
| 862,795 | 8/1907 | Blackiston | 351/155 |
| 2,467,448 | 4/1949 | Vaca | 2/10 |
| 2,538,607 | 1/1951 | Vaca | 2/10 |
| 2,619,641 | 12/1952 | Vaca | 2/10 |
| 2,648,091 | 8/1953 | Jones | 2/10 |
| 2,725,560 | 12/1955 | Feldman | 2/10 |
| 4,152,051 | 5/1979 | Van Tiem et al. | 351/155 |
| 4,304,005 | 12/1981 | Dawley, Sr. | 2/199 |
| 4,541,125 | 9/1985 | Phillips | 2/453 |
| 4,616,367 | 10/1986 | Jean, Jr. et al. | 2/453 |
| 4,636,048 | 1/1987 | Jones | 351/155 |
| 4,781,451 | 11/1988 | McAllen | 351/155 |
| 4,819,274 | 4/1989 | Day | 2/10 |
| 4,863,239 | 9/1989 | Malone | 2/160 |
| 4,885,808 | 12/1989 | Carpenter | 2/453 |
| 4,937,882 | 7/1990 | Hayes | 2/162 |

*Primary Examiner*—Werner H. Schroeder
*Assistant Examiner*—Michael A. Neas
*Attorney, Agent, or Firm*—Leon Gilden

[57] ABSTRACT

An apparatus including a cap structure with an integral forwardly directed brim. The brim includes a first hook and loop fastener strip mounted laterally of the brim to a bottom surface thereof adjacent the cap body portion of the associated cap. The organization includes an eye glass structure including a plurality of spaced hinges mounted to a rigid support plate wherein the rigid support plate includes a second hook and loop fastener strip selectively securable to the first hook and loop fastener strip. Modification of the instant invention further includes a flexible covering flap formed with a forward terminal end and opposed hook and loop fastener strips mounted to each side of the flap adjacent the forward terminal end and cooperative with companion hook and loop fastener strips mounted to upper and lower surfaces of the visor to selectively cover and uncover the eye glass organization dependent on use.

3 Claims, 4 Drawing Sheets

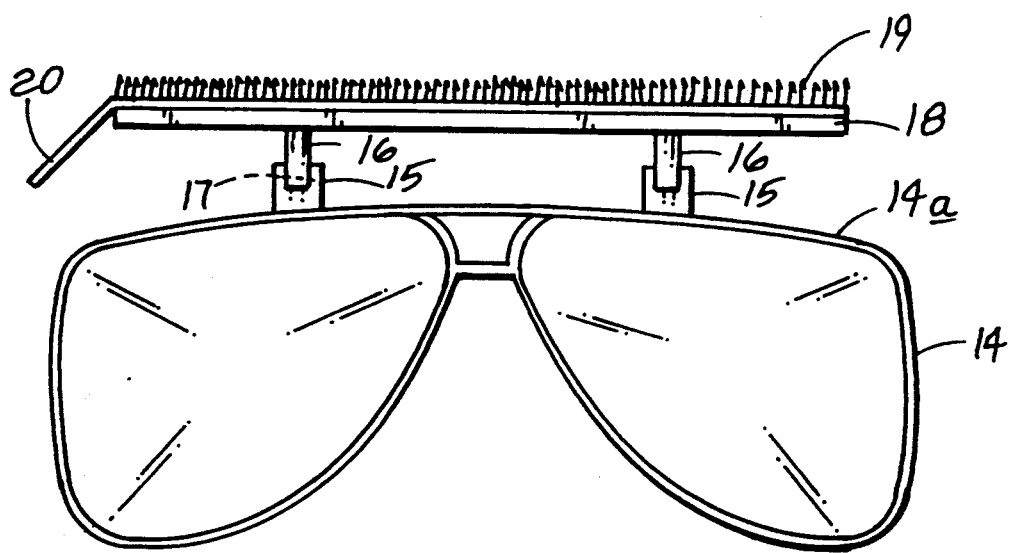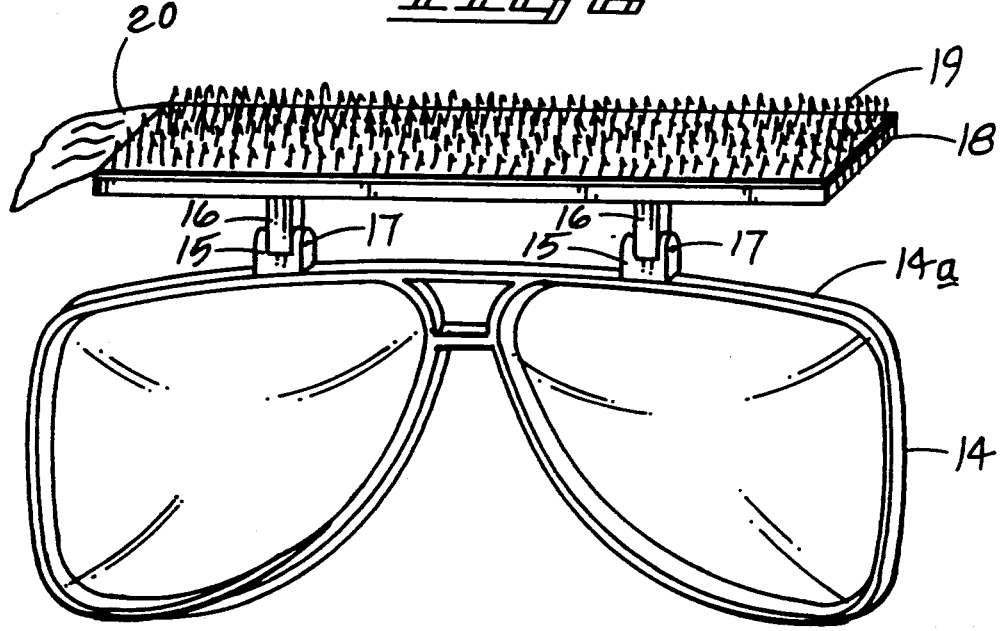

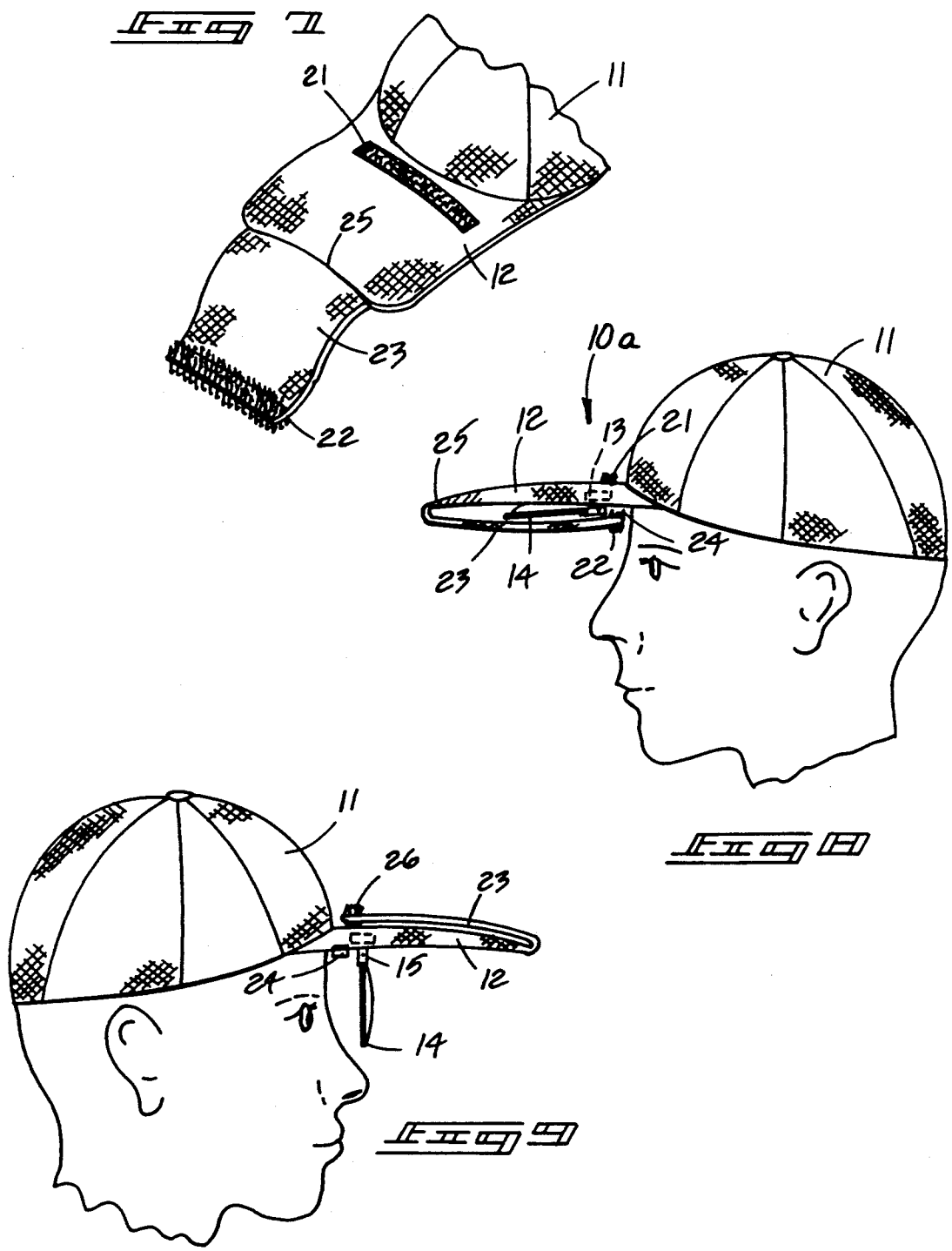

VISOR CAP AND EYE GLASS ORGANIZATION

BACKGROUND OF THE INVENTION

1. Field of the Invention

The field of the invention relates to cap and visor apparatus, and more particularly pertains to a new and improved visor cap and eye glass organization wherein the same permits selective positioning of an eye glass framework relative to a bottom surface of a visor structure to permit selective use of various eye glass types in association with a single cap structure and to further permit selective removal and/or covering of the eyeglass framework.

2. Description of the Prior Art

Visor cap organizations and visor cap organizations in use with eyeglass structure is known in the prior art. Heretofore such combinations have been of either a relatively permanent association or have alternatively utilized cumbersome in relationship to secure an eyeglass structure to an associated visor. Further, in use, it is desirable to permit selective and convenient changing of eyeglass structure depending upon light and optical requirements of an individual utilizing such an organization. Examples of the prior art include U.S. Pat. No. 2,538,607 to Vaca sets forth an eyeglass and cap organization wherein a visor structure is fixedly and hingedly mounted to a bottom surface of a visor cap structure.

U.S. Pat. No. 4,819,274 to Day sets forth a cap with a detachable eye shield wherein the shield is mounted to a block and the block selectively securable to a dovetail groove from the central portion of the underside of the visor member of the cap structure.

U.S. Pat. No. 4,541,125 to Phillips sets forth an eyeglass apparatus for attachment to a cap visor utilizing a unique clip arrangement to selectively secure the visor and a main eye glass portion to the cap structure.

U.S. Pat. No. 2,725,560 to Feldman sets forth a combination cap and eye shield wherein the same utilizes a slotted track and pivot structure of a relatively complex mechanical linking organization to selectively secure an associated eyeglass organization to a cap.

U.S. Pat. No. 2,619,641 to Vaca sets forth a further example of a visor including a slotted U-shaped flange structure to receive a clip organization mounted to an eyeglass framework.

As such, it may be appreciated that there continues to be a need for a new and improved visor cap and eyeglass organization wherein the same addresses both the problems of ease of use as well as effectiveness in construction in permitting the convenient and rapid optical positioning of an eyeglass framework relative to a user thereof and further permits protection of such structure during periods of non-use.

SUMMARY OF THE INVENTION

In view of the foregoing disadvantages inherent in the known types of visor and eyeglass organizations present in the prior art, the present invention provides a new and improved visor cap and eyeglass organization wherein the same permits selective use of an eyeglass structure relative to a visor cap and further permits convenient storage/or removal of the eyeglass organization relative to the cap during periods of non-use. As such, the general purpose of the present invention, which will be described subsequently in greater detail, is to provide a new and improved visor cap and eyeglass organization which has all the advantages of the prior art visor and eyeglass combinations and none of the disadvantages.

To attain this, the visor cap and eyeglass organization of the instant invention essentially includes an apparatus including a cap structure with an integral forwardly directed brim. The brim includes a first hook and loop fastener strip mounted laterally of the brim to a bottom surface thereof adjacent the cap body portion of the associated cap. The organization includes an eye glass structure including a plurality of spaced hinges mounted to a rigid support plate wherein the rigid support plate includes a second hook and loop fastener strip selectively securable to the first hook and loop fastener strip. Modification of the instant invention further includes a flexible covering flap formed with a forward terminal end and opposed hook and loop fastener strips mounted to each side of the flap adjacent the forward terminal end cooperative with companion hook and loop fastener strips mounted to upper and lower surfaces of the visor to selectively cover and uncover the eye glass organization dependent on use.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved visor cap and eyeglass organization which has all the advantages of the prior art visor and eyeglass organizations and none of the disadvantages.

It is another object of the present invention to provide a new and improved visor cap and eyeglass organization which may be easily and efficiently manufactured and marketed.

It is a further object of the present invention to provide a new and improved visor cap and eyeglass organization which is of a durable and reliable construction.

An even further object of the present invention is to provide a new and improved visor cap and eyeglass organization which is susceptible of a low cost of manufacture with regard to both materials and labor, and which accordingly is then susceptible of low prices of sale to the consuming public, thereby making such visor cap and eyeglass organizations economically available to the buying public.

Still yet another object of the present invention is to provide a new and improved visor cap and eyeglass organization which provides in the apparatuses and methods of the prior art some of the advantages thereof, while simultaneously overcoming some of the disadvantages normally associated therewith.

Still another object of the present invention is to provide a new and improved visor cap and eyeglass organization which may be compactly stored when not being utilized.

Yet another object of the present invention is to provide a new and improved visor cap and eyeglass organization wherein the same permits selective positioning, removal, and/or storage of an eyeglass organization relative to a cap and brim structure dependent upon an individual's optical requirements.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is an orthographic frontal view taken in elevation of the eyeglass structure for use in cooperation with the cap and brim structure of the instant invention.

FIG. 6 is an isometric illustration of the eyeglass organization for use with the instant invention.

FIG. 7 is an isometric illustration of a protective flap for use with the cap and brim structure of the instant invention.

FIG. 8 is an orthographic side view taken in elevation of the flap structure as illustrated in FIG. 7 in a protective orientation relative to the eyeglass framework utilized by the instant invention.

FIG. 9 is an orthographic side view taken in elevation of a protective flap as illustrated in FIG. 7 in a moved orientation relative to the eyeglass structure of the instant invention.

DESCRIPTION OF THE PREFERRED EMBODIMENT

Figure 1:
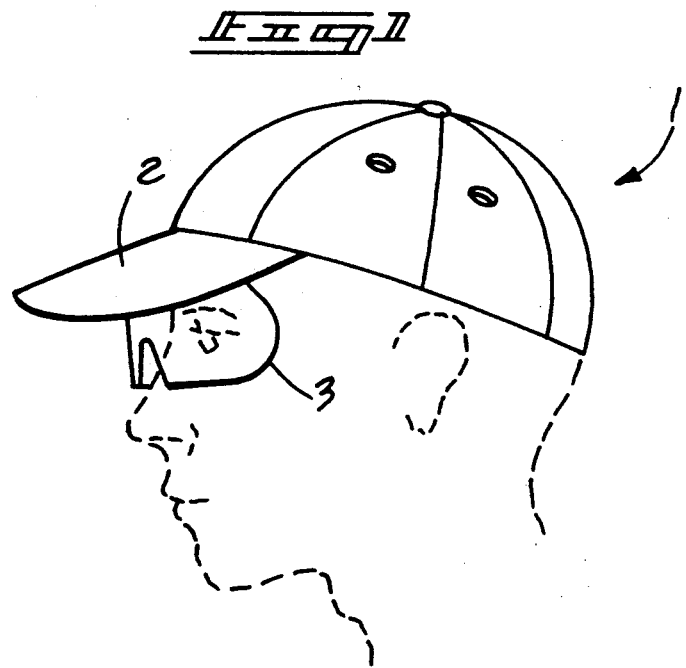
FIG. 1 is an isometric illustration of a prior art visor and eyeglass organization.

With reference now to the drawings, and in particular to FIGS. 1 to 9 thereof, a new and improved visor cap and eyeglass organization embodying the principles and concepts of the present invention and generally designated by the reference numeral 10 will be described.

Figure 2:
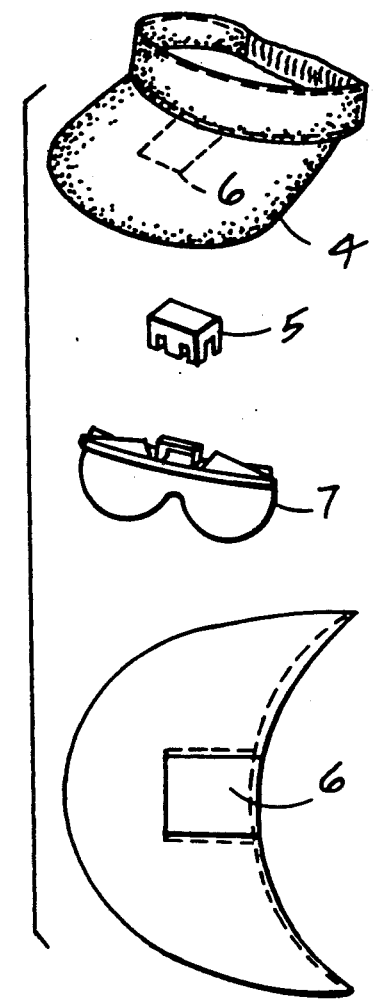
FIG. 2 is an isometric exploded illustration of a further prior art eyeglass and brim structure.
Figure 3:
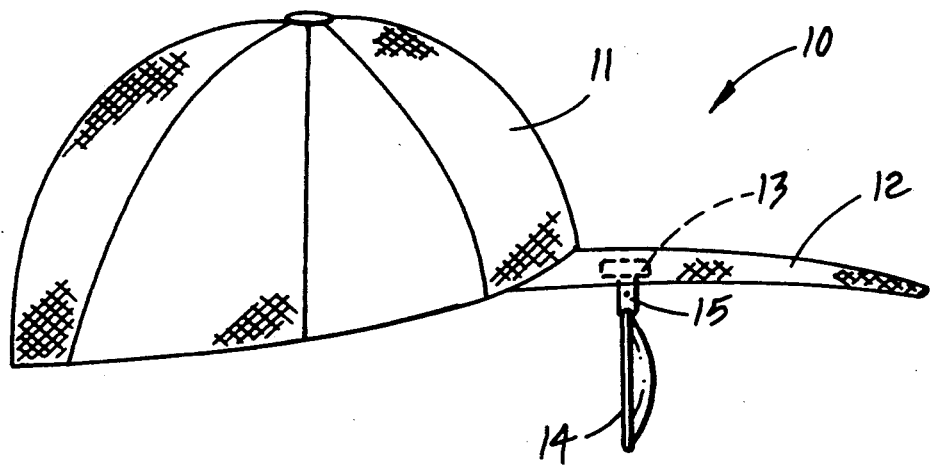
FIG. 3 is an orthographic side view taken in elevation of the instant invention.

FIG. 1 illustrates a cap structure 1 utilizing a forwardly oriented brim 2 with an eyeglass structure 3 arranged for pivoted and integral securement to the visor structure. FIG. 2 is a further example of a prior art visor structure wherein the visor 4 utilizes a dove-tailed slot portion 6 to receive a mounting block 5 that in turn is securable to an eyeglass framework 7.

More specifically, the visor cap and eyeglass organization 10 of the instant invention essentially comprises a cap body including a body portion 11 and a forwardly projecting visor 12.

Figure 4:
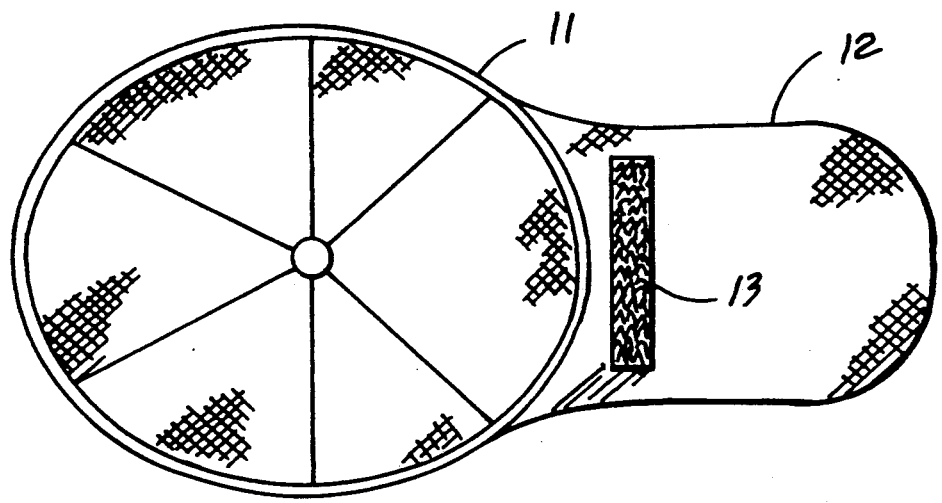
FIG. 4 is a bottom orthographic illustration of the instant invention with the eyeglass framework removed therefrom.

The visor 12 includes a first hook and loop strip 13 integrally mounted to a bottom surface of the visor 12 adjacent an intersection defined between the visor 12 and the body portion 11 and arranged generally laterally of the forward extent of the visor 12 relative to the body portion 11 as illustrated in FIG. 4 for example. An eyeglass frame and associated lenses 14 is provided including a top longitudinal strut 14a. The strut 14a includes a plurality of spaced bifurcated frame members 15 integrally mounted and projecting upwardly of the strut 14. The bifurcated frame members 15 each pivotally mount a frame leg 16 within each respective bifurcated frame member 15. A pivot axle 17 pivotally secures each frame leg 16 to each bifurcated frame member 15. The frame legs 16 are in turn orthogonally and integrally mounted to a bottom surface of a rigid plate body 18. The plate body 18 includes a second hook and loop fastener strip 19 mounted to a top surface thereon. A flexible stripper tab 20 projects laterally of the second hook and loop fastener strip 19 and the plate body 18. The stripper tab 20 permits manual grasping of the tab to permit convenient removal of the eyeglass frame 14 without grasping the framework and soiling the lenses associated therewith.

Clearly selective replacement of various eyeglass frames 14 are provided and permitted dependent upon optical requirements of an individual. For example tinted lenses or various optically ground lenses may be utilized in various frameworks 14 dependent upon requirements of an individual wherein the selective association of the plate body 18 and the second hook and loop fastener strip 19 may be provided in a multitude of such eyeglass frame and lens organizations 14 permitting this convenient interchange. Further, during periods of non-use, the frame 14 may be pivoted relative to the bottom surface of the visor 12 as illustrated in FIG. 8 for example.

FIGS. 7, 8, and 9 illustrate the use of a flexible cover flap 23 cooperative with the visor 12. The cover flap 23 utilizes a hinge 25 coextensively formed along a rear terminal end of the flap 23 and permits hinged mounting of the flap 23 to the visor 12 at a forward terminal end of the visor 12 as illustrated in FIGS. 7 through 8.

A third hook and loop fastener strip 21 is mounted to a top surface of the visor 12 adjacent the body portion 11 and arranged generally downwardly of the visor 12 and generally parallel to the first hook and loop fastener strip 13. A fourth hook and loop fastener strip 22 is mounted to a top surface of the flap 23 while a sixth hook and loop fastener strip 26 is mounted to a bottom surface of the flap 23. A fifth hook and loop fastener strip 24 is mounted rearwardly and parallel to the first hook and loop fastener strip 13 on the bottom surface of the visor 12 as illustrated in FIGS. 8 and 9 for example. In this manner, the flap 23 may selectively provide a protective covering for the frame 14 during periods of non-use of the eyeglass frame 14 and associated lenses while as illustrated in FIG. 9, the flap 23 may be secured to the top portion of the visor 12 by selective securement of the fourth hook and loop fastener strip 22 to the third hook and loop fastener strip 21.

During a covering procedure by the flap 23, the sixth hook and loop fastener strip 26 is mounted to the fifth hook and loop fastener strip 24 while in a storage mode of the flap 23, the fourth hook and loop strap fastener 22 is mounted to a third hook and loop fastener 21.

As to the manner of usage and operation of the instant invention, the same should be apparent from the above disclosure and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A visor cap comprising in combination a cap member including a body portion and a visor extending forwardly of the body portion, the visor including a top surface and a bottom surface and the visor mounted to the body portion at an intersection line, and an eyeglass frame and lens member including a top longitudinal strut, the top longitudinal strut mounted to a rigid plate, and mounting means to permit selective mounting of the rigid plate to the bottom surface of the visor, and wherein the mounting means includes a first hook and loop fastener strip mounted to the bottom surface of the visor adjacent the intersection line and arranged laterally of a forward extent of the visor relative to the body portion, and the rigid plate including a second hook and loop fastener strip selectively securable to the first hook and loop fastener strip, and wherein a flexible stripper tab extends laterally of the rigid plate and the second hook and loop fastener strip is mounted coextensively to a top surface of the rigid plate, and wherein the longitudinal strut includes a plurality of spaced bifurcated frame members, each bifurcated frame member including a frame leg pivotally mounted within each bifurcated frame member, and each frame leg integrally and orthogonally mounted to a bottom surface of the rigid plate to permit pivotment of the longitudinal strut relative to the rigid plate, and a flexible cover flap including a forward flap end and a rear flap end, the rear flap end including a hinge coextensive therewith, and wherein the hinge is mounted at a forward terminal end of the visor, and the flap including a top flap surface and a bottom flap surface, and the top flap surface including a fourth hook and loop fastener strip mounted coextensively with the forward flap end and the bottom flap surface including a sixth hook and loop fastener strip underlying the fourth hook and loop fastener strip and coextensive therewith and contiguous with the forward flap end.

2. A visor cap as set forth in claim 1 further including a third hook and loop fastener strip mounted to the top surface of the visor parallel to the first hook and loop fastener strip and spaced rearwardly thereof.

3. A visor cap as set forth in claim 2 further including a fourth hook and loop fastener strip mounted to the bottom surface of the visor parallel to the first hook and loop fastener strip and spaced rearwardly thereof adjacent the body portion.

* * * * *